United States Patent
Bernardi et al.

(10) Patent No.: US 6,641,579 B1
(45) Date of Patent: *Nov. 4, 2003

(54) APPARATUS AND METHOD FOR ABLATING CARDIAC TISSUE

(75) Inventors: Richard Bruce Bernardi, Wayne, PA (US); Charles B. Shakespeare, Moorestown, NJ (US)

(73) Assignee: Spectrasonics Imaging, Inc., Wayne, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 185 days.

(21) Appl. No.: 09/677,310

(22) Filed: Sep. 29, 2000

(51) Int. Cl.⁷ .............................................. A61B 18/04
(52) U.S. Cl. ............................................. 606/27; 601/3
(58) Field of Search ........................ 601/2–3; 607/101, 607/102, 122; 606/41, 46, 49, 27

(56) References Cited

U.S. PATENT DOCUMENTS

| | | |
|---|---|---|
| 5,295,484 A | 3/1994 | Marcus et al. |
| 5,817,021 A * | 10/1998 | Reichenberger ................ 601/3 |
| 6,383,151 B1 * | 5/2002 | Diederich et al. ............. 601/2 |
| 6,409,720 B1 * | 6/2002 | Hissong et al. ............... 606/27 |

FOREIGN PATENT DOCUMENTS

| | | |
|---|---|---|
| WO | WO 96/29935 | 10/1996 |
| WO | WO 01/13812 A1 | 3/2001 |

OTHER PUBLICATIONS

"The Feasibility of Using Ultrasound for Cardiac Ablation", J.E. Zimmer et al. The Transactions of Biomedical Engineering, vol. 42, No. 9, Sep. 1995.

* cited by examiner

*Primary Examiner*—Lee Cohen
(74) *Attorney, Agent, or Firm*—RatnerPrestia

(57) ABSTRACT

Method and apparatus for destroying aberrant electrical pathways in the myocardium of the heart by creating lesions in the myocardium by ablation of the myocardium with a focused ultrasound beam.

24 Claims, 4 Drawing Sheets

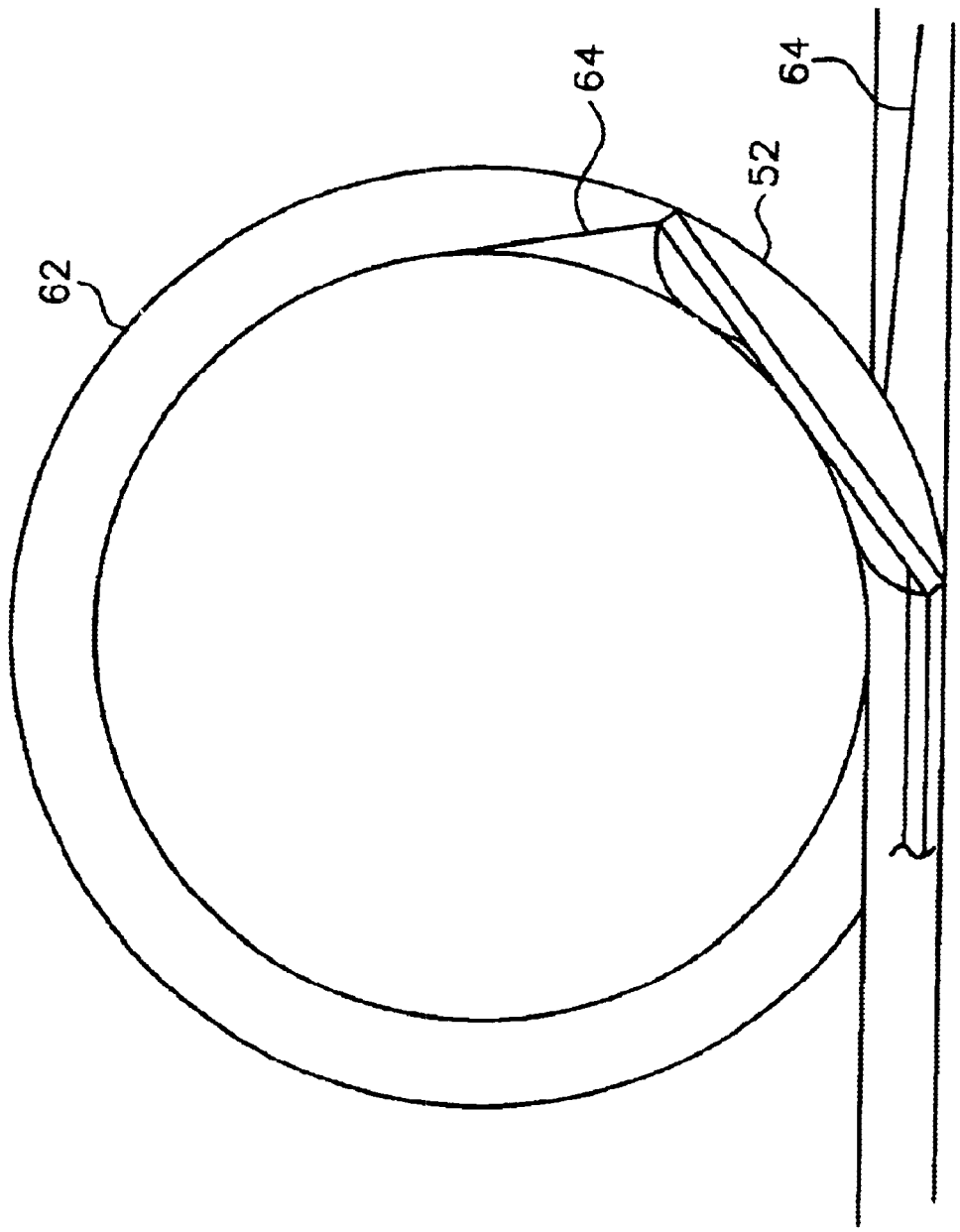

APPARATUS AND METHOD FOR ABLATING CARDIAC TISSUE

TECHNICAL FIELD

The present invention relates, in general, to the treatment of defects in the human heart and, in particular, to destroying aberrant electrical pathways in the myocardium of the heart by creating lesions in the myocardium by ablation of the myocardium.

BACKGROUND OF THE INVENTION

Catheter ablation of cardiac tissue has become widely used in the treatment of symptomatic arrythimias. Cardiac arrythmias occur in areas of the cardiac muscle that have abnormal electrical conduction. This disturbs the propagation of the electrical signals resulting in abnormal muscle contraction. This, in turn, manifests itself in atrial fibrillation or ventricular tachicardia, among other conditions.

It is well known that these arrythmias can be eliminated by interfering with the aberrant electrical conduction pathways that initiate the contraction process. Irreversibly damaging or ablating the pathological tissue regions is one way to achieve this result.

At the present time, however, the only true known cure for atrial fibrillation is a highly invasive surgical procedure known as the "maze" procedure. In the maze procedure, a transmural barrier to aberrant electrical conduction is formed surgically. This procedure, while curative, is so invasive that relatively few are performed annually worldwide.

Currently, the predominant means for generating ablative lesions in the heart is through the use of radio frequency energy. During this type of procedure, the arythmogenic area is mapped and radio frequency energy is delivered from the tip of a catheter that is inserted percutaneously into an artery or a vein. Energy is deposited in the tissue through ionic conduction of electricity, which generates heat in the process. The energy is thermally conducted through the tissue from the source, at the point of contact, in all directions. In the process of creating transmural lesions, volumes of ablated tissue are generated that are far greater in width than necessary or desirable.

For the past five years, electrophysiologists and catheter companies have been working to develop catheters to duplicate the maze procedure or some other set of lesions without the need for open heart surgery. This effort, while still underway, has been largely unsuccessful for a number of reasons, including inadequate contact of the ablating electrode with the myocardium, and technical difficulty of the procedure in creating full thickness (i.e., transmyocardial) continuous lesions.

The desired result of any such ablation equipment is the creation of a lesion deep enough into the myocardium to destroy aberrant electrical pathways, yet limit the amount of collateral damage done to healthy tissue.

Ultrasound offers an energy source that, in many respects, is very well suited for ablation of cardiac tissue in the treatment of symptomatic arrythmias. Because ultrasound is transmitted effectively in both blood and fat, an ultrasound ablation transducer need not be in intimate contact with the myocardium being treated. Also, because ultrasound energy is transmitted as an acoustic wave through most solid and liquid media, ultrasound energy can be focused and manipulated in much the same way as light allowing for the delivery of maximum energy within the cardiac wall.

An important characteristic of acoustic wave transmission in tissue, especially at high frequencies (e.g., 1 to 20 MHz), is that some energy is absorbed as the wave propagates through the tissue. This property permits using acoustic energy to selectively heat tissues to a temperature where the proteins are denatured and cells irreversibly destroyed. It has been demonstrated that by applying ultrasound energy to cardiac tissue for extended periods of time (e.g., up to sixty seconds), tissue can be heated and an ablation lesion can be produced.

SUMMARY OF THE INVENTION

A method for ablation of cardiac tissue in a myocardium, performed in accordance with the present invention, includes the steps of locating a region of aberrant electrical pathways in the myocardium and scanning a focused ultrasound beam through the region of the myocardium to destroy aberrant electrical pathways by creating a lesion of desired extent in the myocardium.

Apparatus for ablation of cardiac tissue in a myocardium, constructed in accordance with the present invention, includes an ultrasound transducer and control means for energizing the ultrasound transducer to transmit a focused ultrasound beam at selected times and for selected periods to selected points in the myocardium to destroy aberrant electrical pathways in the myocardium by creating a lesion of desired extent in the myocardium.

BRIEF DESCRIPTION OF THE DRAWINGS

FIG. 4A is a vertical sectional view of a unit useful in carrying out the method of creating a lesion in the myocardium in accordance with the present invention.

FIG. 4B is a cross-sectional view of the FIG. 4A unit.

DETAILED DESCRIPTION OF THE INVENTION

Figure 1:
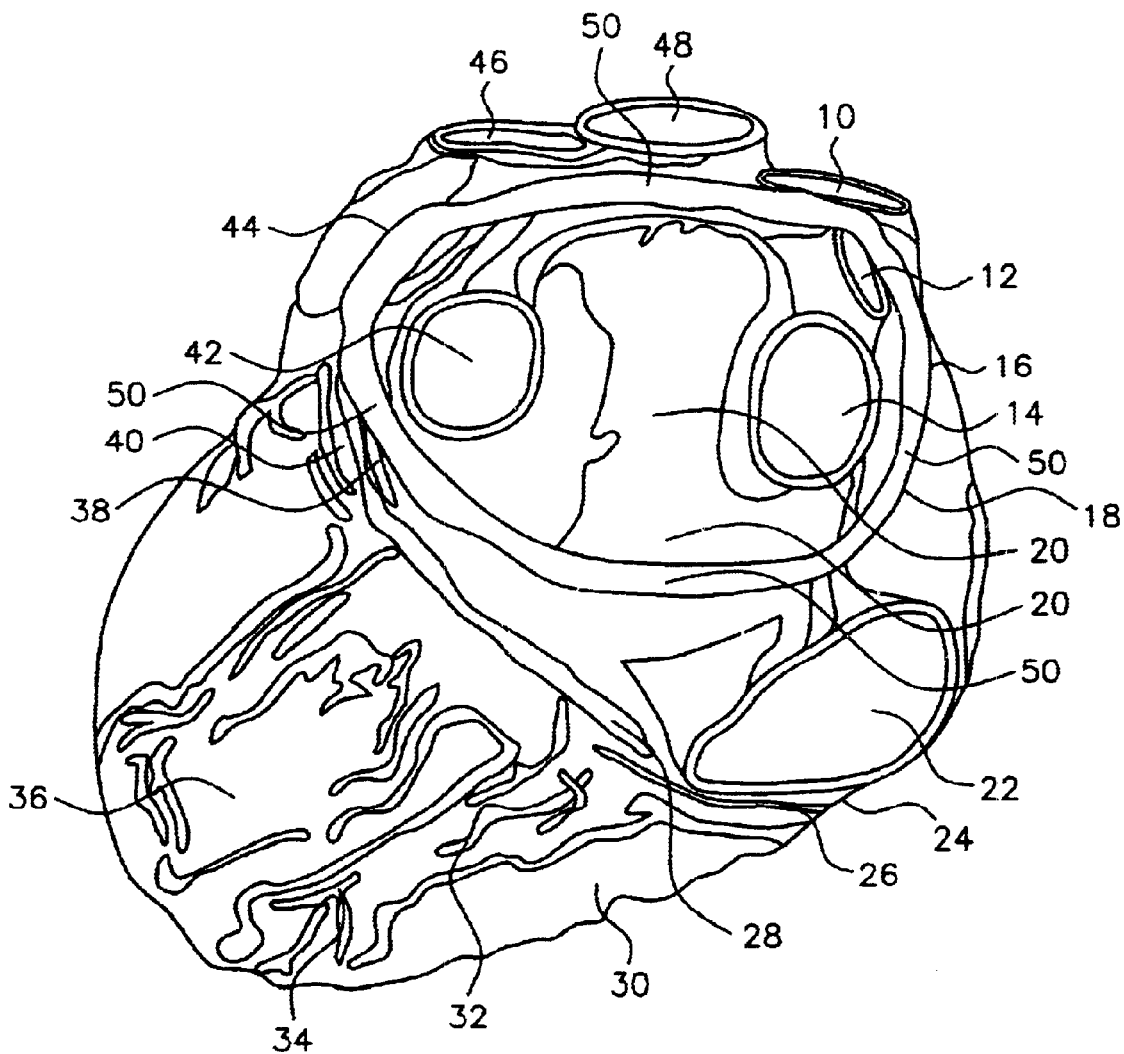
FIG. 1 is a posterior view of a human heart showing a region of the myocardium of the heart through which a focused ultrasound beam is scanned to destroy aberrant electrical pathways by ablation of cardiac tissue and creation of a lesion of desired extent in the myocardium in accordance with the present invention.

Referring to FIG. 1, a human heart has:

a superior vena cava 10
right pulmonary veins 12 and 14
right atrium 16
intra atrial sulcus 18
area of oblique pericardial sinus 20
an inferior vena cava 22
a right coronary artery 24
a small cardiac vein 26
a coronary sinus 28
a right ventricle 30
a posterior interventicular branch 32
a middle cardiac vein 34
a left ventricle 36 an oblique vein 38
a great cardiac vein 40
left pulmonary veins 42
fold of left vena cava 44
a pulmonary trunk 46 and
an aorta 48.

In accordance with the present invention, a region of aberrant electrical pathways in the myocardium is located and a focused ultrasound beam is scanned through this region of the myocardium to destroy aberrant electrical pathways by creating a lesion of desired extent in the myocardium. FIG. 1 shows a path 50 that isolates the right pulmonary veins 12 and 14 and the left pulmonary veins 42 and along which the ultrasound beam is scanned to create the desired lesion in the myocardium by ablation.

Figure 2:
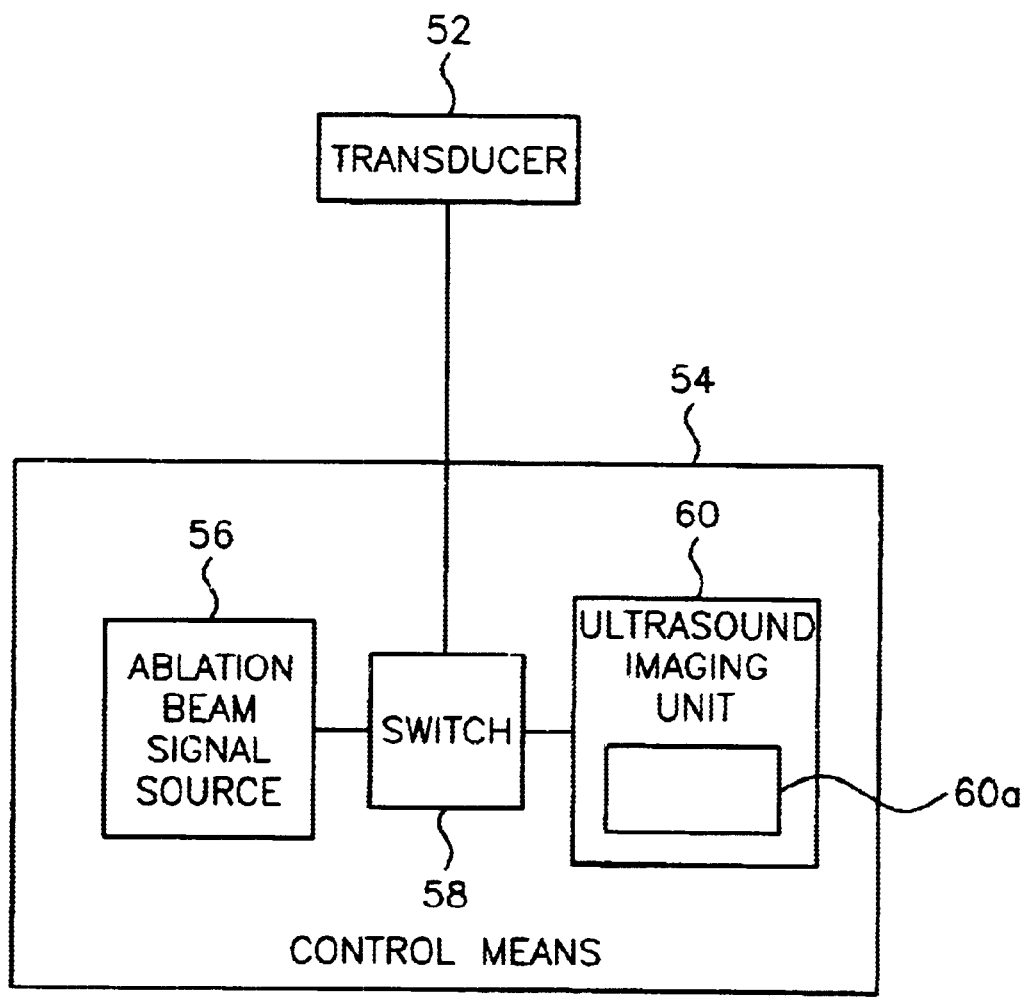
FIG. 2 is a block diagram of apparatus, constructed in accordance with the present invention, for ablation of cardiac tissue in the myocardium to destroy aberrant electrical pathways and creation of a lesion of desired extent in the myocardium in accordance with the present invention.

As shown in FIG. 2, apparatus, constructed in accordance with the present invention, for ablation of cardiac tissue in the myocardium to create the desired lesion includes an ultrasound transducer 52 and control means 54 for energizing ultrasound transducer 52 to transmit a focused ultrasound beam at selected times and for selected periods of time to selected points in a region of the myocardium to create the desired lesion in the myocardium. Ultrasound transducer 52 can be of conventional construction and operation.

The step of scanning the focused ultrasound beam includes moving the focused ultrasound beam to points along scan path 50 at which a plurality of lesions are created that merge to form the lesion of desired extent in the myocardium. As shown in FIG. 2, control means 54 include an ablation beam signal source 56 which generates signals that are coupled to ultrasound transducer 52 through a switch 58 to energize the ultrasound transducer and transmit a focussed ultrasound beam to a target, namely the region of the myocardium where the desired lesion is to be created. The focused ultrasound beam preferably has a duration of less than five seconds at each points along scan path 50. Under these conditions, blood flow itself is not an effective cooling mechanism. By limiting the duration of the ultrasound beam to less than five second, the blood flow will not increase and counteract ablation of the myocardium by the focused ultrasound beam. Typically, the frequency of the focused ultrasound beam will be between 5 MHz and 15 MHz.

Figure 3:
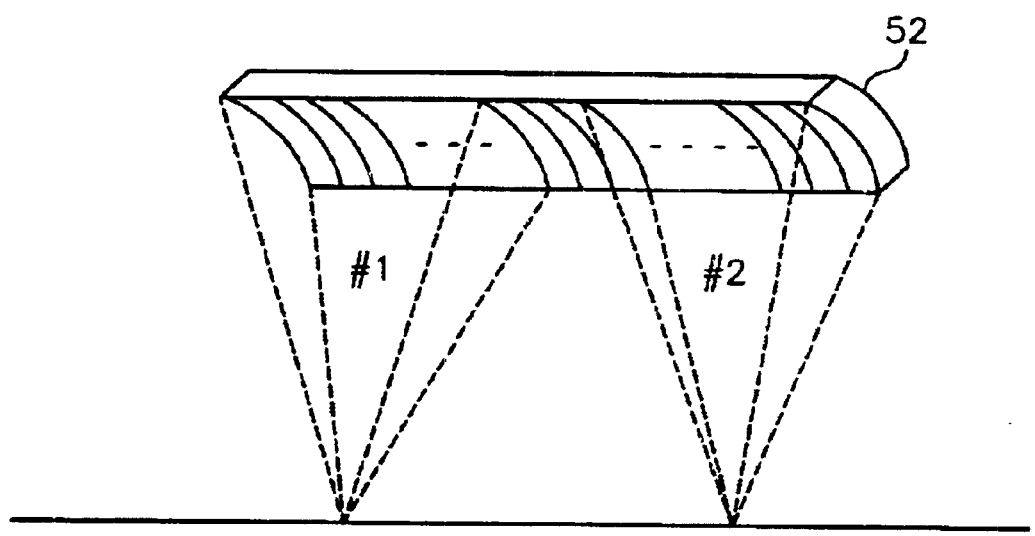
FIG. 3 is a schematic representation of two transmissions of a focussed ultrasound beam by an ultrasound transducer in accordance with the present invention.

FIG. 3 is a schematic representation of two transmissions of a focussed ultrasound beam by an ultrasound transducer 52. As shown, the ultrasound transducer is composed of a plurality of elements that are energized in a timed sequence by signals from ablation beam signal source 56 to form an ultrasound beam that is electronically scanned, in the usual manner, as the different elements of the ultrasound transducer are energized. The scanning mode can be sequential (i.e., groups of transducer elements are energized in physical order), so that a plurality of lesions are created as a sequence of elemental lesions that merge to form the lesion of desired extent in the myocardium. Alternatively, the scanning mode can be other than sequential (i.e., groups of transducer elements are energized in other than physical order or more than one group of transducer elements is energized at the same time), so than the plurality of lesions are not formed in sequence. One reason for non-sequential scanning is to permit the transducer elements to cool down between transmissions when either the power level is high or the time between transmissions is short. The design of ablation beam signal source 56 permits selection of the desired mode of scanning.

The power or intensity level of the focused ultrasound beam can be adjusted, so that only at the focus of the ultrasound beam will the intensity be sufficiently high to irreversibly ablate the myocardium. This allows destroying tissue at depth without damaging overlying structures.

The ablation of the myocardium can be conducted by transmission of the focused ultrasound beam either from the epicardium of the heart or the endocardium of the heart.

Preferably, control means 54 include inspection means for inspecting the lesion created in the myocardium. Such inspection means are particularly useful when the lesions are created by transmissions of the focused ultrasound beam from the endocardium of the heart. The inspection means can be a conventional ultrasound imaging unit 60 that generates signals that are coupled through switch 58 to energize ultrasound transducer 52 to transmit ultrasound signals to a selected target and receives signals conducted through switch 58 from ultrasound transducer 52 that are developed from reflections of the ultrasound signals from the target. Ultrasound imaging unit 60 forms, in the usual manner, an ultrasound image on a display screen 60a of the target, namely the lesion in the myocardium. Thus, the same ultrasound transducer serves to form the focused ultrasound beam that creates the lesions in the myocardium and to develop ultrasound images of the lesions in the myocardium. The operating mode of this ultrasound transducer is determined by the position of switch 58.

As indicated previously, the aberrant electrical pathways are destroyed by a lesion that isolates the right pulmonary veins and the left pulmonary veins from the remainder of the atrium. One such lesion set is the one created along scan path 50 shown in FIG. 1. Other scan paths can be used. For example, two scan paths, one surrounding and isolating the right pulmonary veins and another surrounding and isolating the left pulmonary veins can be used. In any case, the step of scanning the focused ultrasound beam electronically is repeated at selected locations in the selected region or regions of the myocardium as the ultrasound transducer is repositioned manually along the selected scan path.

FIGS. 4A and 4B illustrate one way of manually repositioning the ultrasound transducer along a selected scan path. An ultrasound transducer 52 is positioned in a tube 62 that is adapted to be positioned on the heart. Ultrasound transducer 52 is pulled through tube 62 by a pull wire 64 fastened to the leading end of the ultrasound transducer. Tube 62 is made of a material that is expandable and has the proper acoustic impedance. The tube has sufficient flexibility to form a curved passage but is sufficiently stiff to allow pressure to be applied so as to maintain contact with the beating heart.

Tube 62 is positioned in its unexpanded shape in order to pass through the anatomical confines of the atrium. Preferably, water is passed through tube 62. The pressure of the water passing through tube 62 expands the tube. The water also serves as a coupling material and as a coolant for the ultrasound transducer. After tube 62 has been positioned, ultrasound transducer 52 is inserted in the tube. As shown in FIG. 4B, tube 62 is shaped to prevent rotation of ultrasound transducer 52 relative to the cardiac surface.

Pull wire 64 is indexed, so that ultrasound transducer 52 is properly repositioned at prescribed points along the scan path at which the focused ultrasound beam is scanned electronically to create the desired lesion sequence in the myocardium. The transducer is moved in increments that result in overlap of the plurality of lesions.

It should be noted that instead of using only a single ultrasound transducer, a series of ultrasound transducers can be connected to form a train of ultrasound transducers. Such an arrangement will quicken the ablation process.

Although illustrated and described above with reference to certain specific embodiments, the present invention is nevertheless not intended to be limited to the details shown. Rather, various modifications may be made in the details within the scope and range of equivalents of the claims and without departing from the spirit of the invention.

What is claimed is:

1. A method for ablation of cardiac tissue in the myocardium of the heart comprising the steps of:
    providing an ultrasound transducer having a plurality of elements;
    locating a region of aberrant electrical pathways in the myocardium; and
    selectively energizing said plurality of elements of said ultrasound transducer to:
        (a) form a focused ultrasound beam, and
        (b) scan the ultrasound beam along a scan path extending through said region of the myocardium and along which a plurality of lesions are created that merge to form linear lesions in the myocardium in a plane containing the locus of said ultrasound transducer.

2. The method of claim 1 further including the step of inspecting the linear lesions formed in the myocardium.

3. The method of claim 2 wherein the step of inspecting the linear lesions formed in the myocardium includes forming an ultrasound image of the linear lesions formed in the myocardium.

4. The method of claim 1 wherein the ultrasound beam is transmitted from the epicardium of the heart.

5. The method of claim 4 wherein the focused ultrasound beam is moved in discrete steps to points along a scan path at which the linear lesions are created as a sequence of elemental lesions that merge to form the linear lesions in the myocardium.

6. The method of claim 1 wherein the ultrasound beam is transmitted from the endocardium of the heart.

7. The method of claim 6 wherein the focused ultrasound beam is moved in discrete steps to points along a scan path at which the linear lesions are created as a sequence of elemental lesions that merge to form the linear lesions in the myocardium.

8. The method of claim 1 wherein the duration of the energizing of said plurality of elements of said ultrasound transducer is less than five seconds.

9. The method of claim 8 wherein the focused ultrasound beam has a frequency between 5 MHz and 15 MHz.

10. Apparatus for ablation of cardiac tissue in the myocardium of the heart comprising:
    an ultrasound transducer having a plurality of elements; and
    control means for:
        (a) moving said ultrasound transducer to selected positions along a scan path in a region of the myocardium having aberrant electrical pathways at which a plurality of lesions are to be created, and
        (b) energizing said elements of said ultrasound transducer in timed sequences at selected times and for selected periods of time to:
            (1) transmit a focused ultrasound beam to create a plurality of lesions that merge to form a linear lesion in a plane containing the locus of said ultrasound transducer while said ultrasound transducer is at the selected positions along the scan path, and
            (2) scan the focused ultrasound beam along the scan path to create a plurality of lesions that merge to form a plurality of linear lesions in the myocardium in a plane containing the locus of said ultrasound transducer while said ultrasound transducer is at the selected positions along the scan path.

11. The apparatus of claim 10 wherein said control means include inspection means for inspecting the linear lesions formed in the myocardium.

12. The apparatus of claim 11 wherein said inspection means include an ultrasound imaging unit.

13. The apparatus of claim 12 wherein said ultrasound imaging unit includes:
    (a) means for generating signals that are coupled to said ultrasound transducer to energize said ultrasound transducer to transmit ultrasound signals to a selected target, and
    (b) means for receiving signals from said ultrasound transducer that are developed from reflections of the ultrasound signals from the target.

14. The apparatus of claim 10 wherein said control means scan the focused ultrasound beam in discrete steps to create the plurality of lesions as a sequence of elemental lesions that merge to form the linear lesions in the myocardium.

15. The apparatus of claim 14 wherein said control means include inspection means for inspecting the linear lesions formed in the myocardium.

16. The apparatus of claim 15 wherein said inspection means include an ultrasound imaging unit.

17. The apparatus of claim 16 wherein the selected period of time said control means energize said ultrasound transducer is less than five seconds for each energizing of said ultrasound transducer.

18. The apparatus of claim 16 wherein said control means energize said ultrasound transducer at a frequency between 5 MHz and 15 MHz.

19. The apparatus of claim 16 wherein said ultrasound imaging unit includes:
    (a) means for generating signals that are coupled to said ultrasound transducer to energize said ultrasound transducer to transmit ultrasound signals to a selected target, and
    (b) means for receiving signals from said ultrasound transducer that are developed from reflections of the ultrasound signals from the target.

20. A method for ablation of cardiac tissue in the myocardium of the heart comprising the steps of:
    identifying a region of the myocardium that contains aberrant electrical pathways;
    defining a scanning path that extends along a surface of the myocardium and in which a plurality of lesions are to be created;
    developing a focused ultrasound beam;
    directing the focused ultrasound beam to the scanning path and scanning the focused ultrasound beam along the scanning path while the source of the ultrasound beam is at a first position on the scanning path to create pluralities of lesions that merge to form a first plurality of linear lesions in the myocardium that extend along the scanning path; and
    directing the focused ultrasound beam to the scanning path and scanning the focused ultrasound beam along the scanning path while the source of the ultrasound beam is at a second position on the scanning path to create pluralities of lesions that merge to form a second plurality of linear lesions in the myocardium that extend along the scanning path and overlap the first plurality of linear lesions.

21. The method of claim 20 wherein the focused ultrasound beam is transmitted from the epicardium of the heart.

22. The method of claim 20 wherein the focused ultrasound beam is transmitted from the endocardium of the heart.

23. The method of claim 20 further including the steps of:
   (a) placing a flexible tube along the scanning path,
   (b) placing a source of the focused ultrasound beam in said flexible tube, and
   (c) repositioning said source of the focused ultrasound beam in said flexible tube to change the position of said source of the focused ultrasound beam from the first position on the scanning path to the second position on the scanning path.

24. The method of claim 20 wherein the linear lesions are formed in a plane containing the locus of a source of the focused ultrasound beam.

* * * * *